United States Patent [19]

Nagai et al.

[11] 4,048,236
[45] Sept. 13, 1977

[54] PROCESS FOR PREPARING o-ALKOXY-p-ALLYLPHENOLS

[75] Inventors: Shigeki Nagai; Fumio Iwata; Kenzi Kubo, all of Ube, Japan

[73] Assignee: UBE Industries, Ltd., Ube, Japan

[21] Appl. No.: 658,452

[22] Filed: Feb. 17, 1976

[30] Foreign Application Priority Data

Mar. 7, 1975 Japan .................................. 50-27004
Mar. 7, 1975 Japan .................................. 50-27005
Mar. 7, 1975 Japan .................................. 50-27006

[51] Int. Cl.$^2$ ............................................. C07C 41/00
[52] U.S. Cl. ................................................. 260/613 D
[58] Field of Search ........................ 260/613 D, 624 B

[56] References Cited
FOREIGN PATENT DOCUMENTS 117,492  7/1958  U.S.S.R. ........................... 260/613 D

OTHER PUBLICATIONS

Mel'Kanovitskaya et al., Chem. Abs., vol. 54, (1960) 20,948.
Tsukervanik et al., Byulleten izobreteniy (1959), Nr. 2, p. 27.

Primary Examiner—Bernard Helfin
Attorney, Agent, or Firm—Flynn & Frishauf

[57] ABSTRACT

In a process for preparing an o-alkoxy-p-allylphenol comprising reaction of an o-alkoxyphenol with an allyl halide in the presence of an aqueous solution of an alkali metal hydroxide or alkaline earth metal hydroxide, the improvement which comprises employing a copper-containing compound such as a water-soluble copper salt, an ammine copper complex salt etc., as the catalyst. The process for preparing an o-alkoxy-p-allylphenol which comprises reaction of an o-alkoxyphenol with an allyl halide in an aqueous ammonia is also disclosed.

14 Claims, No Drawings

PROCESS FOR PREPARING o-ALKOXY-p-ALLYLPHENOLS

This invention relates to a process for preparing an o-alkoxy-p-allylphenol. In particular, this invention relates to an improvement in a process for preparing an o-alkoxy-p-allylphenol.

In a known process, an o-alkoxy-p-allylphenol is prepared by reaction of an o-alkoxyphenol with an allyl halide in the presence of an aqueous solution of an alkali metal hydroxide or alkaline earth metal hydroxide, as disclosed in Japanese patent provisional publication No. 14435/74 in which a priority based on U.S. Ser. No. 244,958 is claimed. Although this process can afford the desired o-alkoxy-p-allylphenol, this has defects in that such by-products as a 2-alkoxyphenyl allyl ether(2) and a 2-alkoxy-4-allylphenyl allyl ether(3) are produced in larger amounts as well as the desired o-alkoxy-p-allylphenol(1). In addition to the above defects, a long reaction period (for instance, 100 hours) and low conversion are also disadvantages.

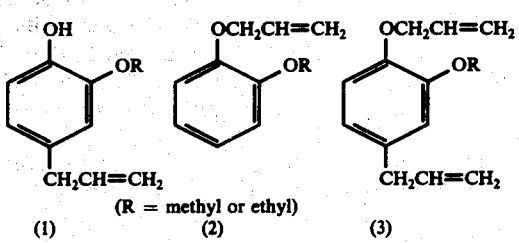

Accordingly, an object of this invention is to provide a new process for preparing an o-alkoxy-p-allylphenol.

Another object of this invention is to provide a process which involves an improvement of the known process for the preparation of an o-alkoxy-p-allylphenol.

A further object of this invention is to provide a process for preparing an o-alkoxy-p-allylphenol which is advantageous in shortening the reaction period required.

A still further object of this invention is to provide a process for preparing an o-alkoxy-p-allylphenol which is advantageous in elevating the conversion based on the starting material and/or selectivity to the desired compound.

Other objects of this invention will be seen from the contents of this specification.

The present invention provides a process for preparing an o-alkoxy-p-allylphenol comprising reaction of an o-alkoxyphenol with an allyl halide in the presence of an aqueous solution of an alkali metal hydroxide or alkaline earth metal hydroxide which is characterized by further employing a copper-containing compound as a catalyst. The copper-containing compound is employed in an amount of 0.01–0.2 gram atom per one mole of the said o-alkoxyphenol.

Throughout the title of the invention, specification and claims of this application, the term "alkoxy" means methoxy or ethoxy.

The allyl halide is preferably used in an amount of 1–1.5 moles per one mole of the o-alkoxyphenol. The allyl halide preferably is allyl chloride of allyl bromide.

The alkali metal hydroxide or alkaline earth metal hydroxide is exemplified by hydroxides of Li, K, Na, Ca, Ba, Mg and Zn. Preferred are hydroxides of potassium and sodium. The said hydroxide is preferably used in an amount of 0.9–1.2 gram equivalents per one mole of the o-alkoxyphenol. The said hydroxide may be introduced into the reaction system in the form of either a solid or solution. In the latter case, there is no limitation on the concentration of the hydroxide solution.

There is no specific limitation on the volume of water which is used as a reaction solvent. However, if the concentration is too low, the reaction rate decreases. Therefore, 200–400 ml of water is preferably used per one mole of the o-alkoxyphenol.

The copper-containing compound includes various compounds which contain copper atoms in the formula. Representatives of the copper-containing compound are water-soluble copper salts, copper oxide or hydroxide, amine copper complex salts and double salts of water-soluble copper salts with ammonium salts.

The water-soluble copper salt is employed in an amount of 0.01–0.1 gram atom, preferably 0.02–0.07 gram atom, per one mole of the o-alkoxyphenol. Examples of the water-soluble copper salt are copper acetate, copper chloride (cuprous chloride and cupric chloride), copper nitrate, copper sulfate, copper phosphate, copper carbonate, copper borate and copper silicate. Of these salts, cuprous chloride, cupric chloride, cuprous bromide, cupric bromide and copper(II) sulfate are preferred.

The reaction temperature is from 10° to 95° C, preferably from 25° to 50° C. If a lower temperature than the above lower limit is used, the reaction rate decreases. Higher temperatures than the above upper limit favor side-reactions.

There is no specific limitation on the order for adding the reactants and other substances, that is, an o-alkoxyphenol, an allyl halide, an alkaline material and a water-soluble copper salt. According to one embodiment, an alkaline substance and a water-soluble copper salt are firstly dissolved in water, and to this solution are added an o-alkoxyphenol and an allyl halide. The resulting mixture is heated with stirring to elevate the temperature. According to another embodiment, an o-alkoxyphenol, an allyl halide and a water-soluble copper salt are firstly added to water. Then, after adding an alkaline substance, the resulting mixture is heated with stirring to elevate its temperature.

In the above-mentioned reaction system, an ammonium salt may also be added, so that the conversion and/or selectivity to the desired compound are further improved.

The ammonium salt may be an organic or inorganic one. In the latter case, salts of strong and weak acids may be both employed. Examples of the ammonium salt are as follows: ammonium sulfite, ammonium hydrogenphosphite, ammonium chloride, ammonium chlorate, ammonium perchlorate, ammonium carbonate, ammonium hydrogencarbonate, ammonium thiosulfate, ammonium metavanadate, ammonium methaborate, ammonium sulfate, ammonium hydrogensulfate, ammonium phosphate, ammonium hydrogenphosphate and ammonium acetate. The ammonium salt is preferably employed in an amount of from 1 to 4 moles, more preferably from 1 to 2 moles, of the ammonium portion per one gram atom of the copper.

When the copper salt is present with an ammonium salt in the system, a double salt may be formed in certain cases. This assumption may be proved by two experiments giving almost the same result. One is conducted using a double salt, copper(II) chloride - ammonium(-

$CuCl_2 \cdot 2NH_4Cl \cdot 2H_2O$), and another is conducted using $CuCl_2 \cdot 2H_2O$ and ammonium chloride both in such an amount that the double salt may be just formed in theory.

Accordingly, a double salt of a water-soluble copper salt with an ammonium salt may be employed in place of using both a water-soluble copper salt and an ammonium salt. An amount of the copper contained in the double salt preferably is 0.05–0.1 gram atom per one gram equivalent of the alkali metal hydroxide or alkaline earth metay hydroxide. The components and an amount of the double salt are the same as mentioned above or directly calculated from the above-mentioned amounts.

When an ammonium salt or the double salt is involved, the reaction temperature is from 0° to 60° C, preferably from 20° to 35° C. The reaction period is from 5 to 180 minutes, preferably from 10 to 60 minutes.

Alternatively, ammonia may be present in the system in place of the ammonium salt. When the ammonia is present with the copper salt in the system, an amine copper complex salt may be formed in a certain case. This assumption may be proved by occurrence of color indicating a complex formation when ammonia and a copper salt are introduced into the system. Therefore, ammonia is added in at least one molar amount per one gram atom of the copper. From 2 to 4 moles of ammonia are preferably used per one gram atom of the copper.

Accordingly, an ammine copper complex salt may be employed in place of combination of the copper salt and ammonia. Examples of the ammine copper complex salt are as follows:

$[Cu^I(NH_3)]X$, $[Cu^I(NH_3)_2]X$, $[Cu^{II}(NH_3)_2]X_2$, $[Cu^I(NH_3)_3]X$, $[Cu^{II}(NH_3)_4]X_2$, $[Cu^{II}(NH_3)_6]X_2$, (X is a halogen atom)

The complex salts used in this process are not limited to the above-listed complex salts. For instance, X may be OH, $NO_3$ or $ClO_4$, and $X_2$ may be $(OH)_2$, $(NO_3)_2$, $(ClO_4)_2$ or $SO_4$.

In this process, there is no specific limitation on the order for adding the reactants and other substances. The embodiments mentioned hereinbefore may be applied to this reaction with some necessary modifications.

The reaction which involves a water-soluble copper salt and ammonia, or an ammine copper complex salt is ordinarily carried out at a temperature of from 0° to 50° C, preferably from 10° to 25° C. Temperatures outside the above-mentioned range will cause the same troubles as stated hereinbefore. The reaction period is from 5 to 180 minutes, preferably from 10 to 30 minutes.

Where an ammine copper complex salt is employed, it is used in 0.01–0.2 molar amount, preferably 0.05–0.1 molar amount, per one mole of the o-alkoxyphenol. The said complex salt may be used in a greater amount than the above-mentioned range.

Further, a certain nitrogen-containing compound may be present in the system in place of the aforementioned ammonium salt. The said nitrogen-containing compound is selected from the group consisting of an amine, a hydrazine, an amide and an amino acid.

The amine used in this process may be hydroxylamine, allylamine, an alkylamine containing 1–4 carbon atoms, an alkoxyalkylamine containing 2–4 carbon atoms or ethylenediamine, and is exemplified by hydroxylamine, methylamine, ethylamine, n-propylamine, isopropylamine, allylamine, 2-methoxyethylamine and ethylenediamine. The amide may have 1–4 carbon atoms and is exemplified by formamide, acetamide and propionic amide. The hydrazine may have 0–4 carbon atoms and is exemplified by hydrazine, N-methylhydrazine and N-ethylhydrazine. The amino acid is exemplified by glycine, α-alanine, β-alanine, γ-amino-n-butyric acid, δ-amino-n-valeric acid, ε-aminocaproic acid, valine, leucine, serine, threonine, cystine, aspartic acid, glutamic acid, lysine, α,γ-diaminobutyric acid and ornithine.

The said nitrogen-containing compound is preferably used in 1–10 molar amounts, more preferably 2–8 molar amounts, per 1 gram atom of the copper.

The reaction is carried out at a temperature of from 0° to 60° C, preferably from 10° to 40° C. The reaction period is from 5 to 240 minutes, preferably from 10 to 120 minutes.

The copper-containing compound may be a hydroxide or oxide of copper, such as $Cu(OH)_2$, $Cu_2O$ or $CuO$. An amount of the copper contained in the hydroxide or oxide of copper is 0.01–0.1 gram atom per one mole of the o-alkoxyphenol. In this case, ammonia may be further added so that the conversion and/or selectivity to the desired compound are further improved. There is no specific limitation on the amount of ammonia. The said ammonia may be introduced in the form of aqueous ammonia.

Separation of the compounds obtained by the aforementioned various processes is preferably carried out in the manner shown below.

A METHOD

The resulting reaction solution was neutralized with a mineral acid and extracted with an organic solvent such as ether, benzene, carbon tetrachloride, chloroform, petroleum ether and methyl isobutyl ketone. The extract containing whole portions of the organic substances is then distilled to separate each component.

B METHOD

The resulting reaction solution was, without being neutralized, extracted with such an organic solvent as stated in the A method. The extract containing the unreacted allyl halide, the desired o-alkoxy-p-allylphenol, by-product 2-alkoxyphenyl allyl ether and a small amount of high-boiling compounds such as 2-alkoxy-4-allylphenyl allyl ether is then distilled to separate each component. The aqueous layer obtained upon extraction is then neutralized with a mineral acid and extracted with the same organic solvent. The resulting extract containing the unreacted o-alkoxyphenyl and a small amount of high-boiling compounds is distilled to separate each component.

The present invention also provides a process for preparing an o-alkoxy-p-allylphenol comprising reaction of an o-alkoxyphenyl with an allyl halide in an aqueous ammonia.

The allyl halide is preferably used in an amount of 1–1.5 moles per one mole of the o-alkoxyphenol. The allyl halide preferably is allyl chloride or allyl bromide.

Ammonia is preferably employed in 0.9–6.0 molar amounts, more preferably in 2.0–4.0 molar amounts, per one mole of the o-alkoxyphenol. Ammonia is preferably used in the form of 10–28 weight percent aqueous solutions. If the reaction is carried out in an extremely dilute ammonia solution, the reaction rate decreases. Therefore, the concentration of ammonia added is advantageously chosen so that 60–300 ml of water per one mole of the o-alkoxyphenol may be present in the system.

When an o-alkoxyphenol and an allyl halide are reacted in an aqueous ammonia, selectivity to the o-alkoxy-p-allylphenol is improved as compared with that in the known process involving an aqueous alkali or alkaline earth metal hydroxide solution. Though, if a copper-containing compound is present in the aqueous ammonia system, the selectivity is improved further, and in addition the reaction period is shortened.

The above-mentioned copper-containing compound is required to be soluble in water even though in a small amount, and should be selected from the aforementioned copper-containing compounds such as a water-soluble copper salt.

An amount of the copper-containing compound may be 0.01–0.1 gram atom, preferably 0.02–0.07 gram atom, per one atom of the o-alkoxyphenol.

The reaction is carried out at a temperature of from 10° to 50° C, preferably from 25° to 40° C. Temperatures outside the above-mentioned range will cause the same troubles as stated hereinbefore. The reaction period is from 1 to 100 hours, preferably from 3 to 50 hours.

Separation of the resulting compounds may be carried out in the manner as stated in the aforementioned A and B methods. In addition, the following methods may be employed as well.

C METHOD

The resulting reaction solution is directly distilled to recover the ammonia and to obtain each of the unreacted compounds and the products separately.

D METHOD

The resulting reaction solution is firstly heated to remove and recover the ammonia. The remaining solution is then extracted with an organic solvent as stated in the A method. The extract is distilled to obtain separately the unreacted compounds and the products.

As detailedly stated hereinbefore, according to the present invention, an o-alkoxy-p-allylphenol which can be used as the starting compound for preparing perfumes, pharmaceuticals etc. is obtained in good yields, that is, excellent in improving the conversion and/or selectivity to the o-alkoxy-p-allylphenol. Further, the reaction period is shortened.

The present invention will be illustrated by the following examples, with reference to the comparative examples. These examples are not intended to limit the present invention.

EXAMPLE 1

To 30 ml of water were added in order 3.22 g of sodium hydroxide, 10 g of guaiacol(o-methoxyphenol), 0.686 g of cupric chloride($CuCl_2 \cdot 2H_2O$; catalyst) and 6.90 g of allyl chloride. The reaction took place at 25° C and with stirring, for 24 hours. The reaction solution was then neutralized with hydrochloric acid and extracted with five portions of 30 ml of ether. The resulting ethereal extract was distilled to give 3.37 g of the desired eugenol (namely, 4-allyl-2-methoxyphenol) and 2.52 g of the unreacted guaiacol. There was also obtained 3.04 g of by-product O-allylguaiacol.

The conversion was 74.8%, and selectivity to eugenol was 34.1%.

COMPARATIVE EXAMPLE 1

The procedure stated in Example 1 was repeated except that no cupric chloride was added.

The conversion was 50.5%, and selectivity to eugenol was 33.7%.

EXAMPLES 2–5

The procedure stated in Example 1 was repeated except that each of the salts set out in Table 1 was employed as the catalyst. The results are shown in Table 1.

Table 1

| Ex. | Catalyst | (amount (g)) | Conversion (%) | Selectivity to eugenol (%) |
|---|---|---|---|---|
| 2 | $CuBr_2$ | 0.897 | 75.1 | 33.2 |
| 3 | $CuSO_4 \cdot 5H_2O$ | 1.407 | 68.0 | 34.0 |
| 4 | CuCl | 0.239 | 77.0 | 34.0 |
| 5 | $Cu(OH)_2$ | 0.234 | 72.5 | 34.2 |

EXAMPLE 6

The procedure stated in Example 1 was repeated except that 83° C reaction temperature and 3 hours of the reaction period were employed.

The conversion was 92.8%, and selectivity to eugenol was 27.0%.

COMPARATIVE EXAMPLE 2

The procedure stated in Example 6 was repeated except that no catalyst was added.

The conversion was 80.9%, and selectivity to eugenol was 27.0%.

EXAMPLE 7

The procedure stated in Example 1 was repeated except that 10.74 g of allyl bromide and 4.98 g of potassium hydroxide were employed in place of the allyl chloride and the sodium hydroxide and that 3 hours reaction period was employed.

The conversion was 93.4%, and selectivity to eugenol was 34.8%.

COMPARATIVE EXAMPLE 3

The procedure stated in Example 7 was repeated except that no catalyst was added.

The conversion was 73.1%, and selectivity to eugenol was 37.7%.

EXAMPLE 8

To 34 ml of water were added in order 3.36 g of sodium hydroxide, 11.60 g of o-ethoxyphenol, 0.716 g of cupric chloride ($CuCl_2 \cdot 2H_2O$; catalyst) and 7.07 g of allyl chloride. The reaction took place at 83° C and with stirring, for 3 hours. The reaction solution was then neutralized with hydrochloric acid and extracted with five portions of 30 ml of ether. The resulting ethereal extract was distilled to give 4.51 g of the desired o-ethoxy-p-allylphenol and 0.78 g of the unreacted o-ethoxyphenol. There was also obtained 6.56 g of by-product 1-allyloxy-2-ethoxybenzene.

The conversion was 93.3%, and selectivity to o-ethoxy-p-allylphenol was 32.3%.

COMPARATIVE EXAMPLE 4

The procedure stated in Example 8 was repeated except that no catalyst was added.

The conversion was 83.3%, and selectivity to o-ethoxy-p-allylphenol was 26.7%.

EXAMPLE 9

A mixture of 10 g of guaiacol, 3.22 g of sodium hydroxide, 6.90 g of allyl chloride, 0.399 g of CuCl, 1.0 g of 28% aqueous ammonia and 34 ml of water was reacted at 25° C and with stirring, for 15 minutes. When the CuCl and aq. ammonia were introduced, a deep blue color occurred, indicating formation of $[Cu^I(NH_3)_2]^+$ ion. The reaction solution was then neutralized with hydrochloric acid and extracted with five portions of 30 ml of ether. The resulting ethereal extract was distilled to give 6.68 g of the desired eugenol and 2.43 g of the unreacted guaiacol. There was also obtained 2.24 g of by-product O-allylguaiacol.

The conversion was 75.7%, and selectivity to eugenol was 66.7%.

COMPARATIVE EXAMPLE 5

The procedure stated in Example 9 was repeated except that neither CuCl nor aqueous ammonia was added.

The conversion was 1.4%, and selectivity to eugenol was 33%.

EXAMPLES 10-14

The procedure stated in Example 9 was repeated except that the reactant and the conditions set out in Table 2 were employed. The results are shown in Table 3.

Table 2

| Ex. | Copper salt | (amount (g)) | Amount (g) of aqueous ammonia | Reaction temperature (° C) |
|---|---|---|---|---|
| 10 | CuCl | 0.399 | 2.2 | 25 |
| 11 | CuCl$_2$ . 2H$_2$O | 0.685 | 1.9 | 25 |
| 12 | " | 0.137 | 0.4 | 40 |
| 13 | " | 1.370 | 4.1 | 25 |
| 14 | CuSO$_4$ . 5H$_2$O | 2.010 | 3.7 | 25 |

Note) When a copper (I) compound and aq. ammonia were introduced, a deep blue color occurred, indicating formation of $[Cu^I(NH_3)_2]^+$ ion, and when copper (II) compound and aq. ammonia were introduced, a violet-blue color occurred, indicating formation of $[Cu^{II}(NH_3)_4]^{2+}$ ion.

Table 3

| Ex. | Conversion (%) | Selectivity to eugenol (%) |
|---|---|---|
| 10 | 74.9 | 67.7 |
| 11 | 84.0 | 53.4 |
| 12 | 75.0 | 52.3 |
| 13 | 81.8 | 54.5 |
| 14 | 85.0 | 60.3 |

EXAMPLE 15

The procedure stated in Example 9 was repeated except that 0.495 g of solid bisammine copper(I) chloride [Cu$^I$(NH$_3$)$_2$]Cl was added in place of adding the CuCl and aqueous ammonia.

The conversion was 77.5%, and selectivity to eugenol was 65.9%.

EXAMPLES 16-20

The procedure stated in Example 9 was repeated except that 10.74 g of allyl bromide and 4.98 g of potassium hydroxide were employed in place of the allyl chloride and sodium hydroxide and that the reactants and the conditions set out in Table 4 were employed. The results are shown in Table 4.

Table 4

| Ex. | Copper-containing compound | (amount (g)) | Amount (g) of aq. ammonia | Conversion (%) | Selectivity to eugenol (%) |
|---|---|---|---|---|---|
| 16 | CuCl | 0.399 | 1.1 | 78.4 | 63.5 |
| 17 | CuCl$_2$ . 2H$_2$O | 0.685 | 1.9 | 76.6 | 63.8 |
| 18 | Cu$_2$O | 0.288 | 1.8 | 79.5 | 60.1 |
| 19 | Cu(CH$_3$COO)$_2$ | 0.729 | 3.6 | 50.3 | 62.4 |
| 20 | Cu$_3$(PO$_4$)$_2$ . 3H$_2$O | 0.575 | 3.6 | 80.4 | 59.5 |

Note) The same color formation as in Examples 9 – 14 was found.

EXAMPLE 21

The procedure stated in Example 11 was repeated except that 11.60 g of o-ethoxyphenol, 6.85 g of allyl chloride and 3.36 g of sodium hydroxide were employed in place of the counterparts used in Example 11.

The conversion was 75.0%, and selectivity to o-ethoxy-p-allylphenol was 60.9%.

COMPARATIVE EXAMPLE 6

The procedure stated in example 21 was repeated except that neither CuCl$_2$.2H$_2$O nor aqueous ammonia was added.

The conversion was 1.3%, and selectivity to o-ethoxy-p-allylphenol was 60.9%.

EXAMPLE 22

The procedure stated in Example 15 was repeated except that 4.27 g of sodium carbonate was employed in place of the sodium hydroxide and that 0.961 g of [Cu$^{II}$(NH$_3$)$_4$]CL$_2$.2H$_2$O was employed as the catalyst.

The conversion was 30.1%, and selectivity to eugenol was 59.5%.

COMPARATIVE EXAMPLE 7

The procedure stated in Example 22 was repeated except that no catalyst was added.

The conversion was 0.9%, and no eugenol was obtained.

EXAMPLE 23

The procedure stated in Example 22 was repeated except that 5.55 g of potassium carbonate was employed in place of the sodium carbonate.

The conversion was 32.7%, and selectivity to eugenol was 59.9%.

EXAMPLES 24-25

The procedure stated in Example 15 was repeated except that an ammine copper complex salt set out in Table 5 was employed in place of the bisammine copper(I) chloride.

Table 5

| Ex. | Complex salt (amount (g)) | Conversion (%) | Selectivity to eugenol (%) |
|---|---|---|---|
| 24 | [Cu$^{II}$(NH$_3$)$_4$]SO$_4$ . H$_2$O 0.992 | 72.3 | 60.7 |
| 25 | [Cu$^{II}$(NH$_3$)$_4$](NO$_3$)$_2$ 1.035 | 71.8 | 58.8 |

EXAMPLE 26

A mixture of 10.00 g of guaiacol, 3.22 g of sodium hydroxide, 6.80 g of allyl chloride, 1.37 g of cupric chloride(CuCl$_2$.2H$_2$O), 1.72 g of ammonium chloride and 30 ml of water was reacted at 25° C and with stirring, for 15 minutes. The reaction solution was then neutralized with hydrochloric acid and extracted with five portions of 30 ml of ether. The ethereal extract was distilled to give 4.70 g of desired eugenol and 4.73 g of the unreacted guaiacol. There was also obtained 1.48 g of by-produced O-allylguaiacol.

The conversion was 52.7%, and selectivity to eugenol was 67.5%.

COMPARATIVE EXAMPLE 8

A mixture of 10.00 g of guaiacol, 3.22 g of sodium hydroxide, 6.80 g of allyl chloride and 30 ml of water was reacted at 25° C and with stirring, for 15 minutes. The reaction solution was then neutralized with hydrochloric acid and extracted with five portions of 30 ml of ether. The ethereal extract was distilled to give 0.07 g of the desired eugenol and 9.83 g of the unreacted guaiacol. There was also obtained 0.10 g of by-product O-allylguaiacol.

The conversion was 1.7%, and selectivity to eugenol was 32.4%.

EXAMPLES 27-39

The procedure stated in Example 26 was repeated except that the reactants and conditions were replaced in the manner as set out in Table 6. The results are shown in Table 6. The data obtained in Comparative example 8 and Example 26 are also set out.

Table 6

| | Products | | | Catalysts | | | |
|---|---|---|---|---|---|---|---|
| Ex. | Unreacted guaiacol(g) (Conversion (%)) | Eugenol(g) (Selectivity (%)) | O-allyl-guaiacol (g) (Selectivity (%)) | Copper salt(g) | Ammonium salt(g) | A | B |
| Comp. Ex. 8 | 9.83 (1.7) | 0.07 (32.4) | 0.100 (44.7) | none | — | — | — |
| Ex.26 | 4.73 (52.7) | 4.70 (67.5) | 1.48 (21.3) | CuCl$_2$ . 2H$_2$O 1.37 | NH$_4$Cl 1.72 | $\frac{1}{10}$ | 4.0 |
| 27 | 6.73 (33.0) | 2.77 (63.1) | 1.05 (23.9) | CuCl$_2$ . 2H$_2$O 1.37 | (NH$_4$)$_2$SO$_4$ 3.89 | $\frac{1}{10}$ | 4.0 |
| 28 | 7.68 (23.2) | 2.09 (68.0) | 0.60 (26.1) | CuCl$_2$ . 2H$_2$O 1.37 | (NH$_4$)$_2$CO$_3$ 2.83 | $\frac{1}{10}$ | 4.0 |
| 29 | 3.77 (62.3) | 5.41 (65.6) | 1.75 (21.2) | CuCl$_2$ . 2H$_2$O 1.37 | NH$_4$CO$_2$CH$_3$ 2.49 | $\frac{1}{10}$ | 4.0 |
| 30 | 5.77 (42.3) | 3.76 (67.2) | 1.27 (22.8) | CuCl$_2$ . 2H$_2$O 1.37 | (NH$_4$)$_3$PO$_4$ . 3H$_2$O 2.18 | $\frac{1}{10}$ | 4.0 |
| 31 | 3.30 (67.0) | 5.82 (65.7) | 1.99 (22.4) | CuCl$_2$ . 2H$_2$O 1.37 CuCl$_2$ . 2NH$_4$Cl . 2H$_2$O *1 2.24 | | $\frac{1}{10}$ *2 | |
| 32 | 3.97 (60.3) | 5.48 (68.7) | 1.84 (23.0) | | NH$_4$Cl 1.72 | $\frac{1}{10}$ | 4.0 |
| 33 | 4.52 (55.0) | 4.89 (67.7) | 1.51 (20.8) | CuSO$_4$ . 5H$_2$O 2.01 | NH$_4$Cl 1.72 | $\frac{1}{10}$ | 4.0 |
| 34 | 4.08 (59.2) | 5.14 (65.7) | 2.02 (25.8) | CuCl 0.80 | (NH$_4$)$_2$SO$_4$ 2.13 | $\frac{1}{10}$ | 4.0 |
| 35 | 3.17 (68.3) | 5.49 (60.8) | 1.55 (17.2) | CuSO$_4$ . 5H$_2$O 2.01 | (NH$_4$)$_2$SO$_4$ 2.13 | $\frac{1}{10}$ | 4.0 |
| 36 | 2.91 (71.0) | 6.11 (65.1) | 2.02 (21.5) | CuCl$_2$ . 2H$_2$O 1.37 | NH$_4$Cl 0.86 | $\frac{1}{10}$ | 2.0 |
| 37 | 5.06 (49.4) | 3.76 (57.4) | 0.97 (14.8) | CuCl$_2$ . 2H$_2$O 1.37 | NH$_4$Cl 3.44 | $\frac{1}{10}$ | 8.0 |
| 38 | 4.25 (57.5) | 4.96 (65.2) | 1.96 (25.7) | CuCl$_2$ . 2H$_2$O 1.37 | NH$_4$Cl 0.57 | $\frac{1}{30}$ | 4.0 |
| 39 | 3.93 (60.8) | 5.18 (64.4) | 1.61 (20.0) | CuCl$_2$ . 2H$_2$O 0.46 CuCl 1.60 | NH$_4$Cl 1.72 | $\frac{1}{5}$ | 2.0 |

Note)
A: Copper salt/Guaiacol (molar ratio)
B: Ammonium salt/Copper salt (molar ratio)
*1: Double salt
*2: Double salt/Guaiacol (molar ratio)

EXAMPLES 40–42

The procedure stated in Example 26 was repeated except that an alkali set out in Table 7 was employed in place of the sodium hydroxide. The results are shown in Table 7.

Table 7

| | | Products | | | Catalysts | | | |
|---|---|---|---|---|---|---|---|---|
| Ex. | Alkali (amount (g)) | Unreacted guaiacol(g) (Conversion (%)) | Eugenol(g) (Selectivity (%)) | O-allyl-guaiacol(g) (Selectivity (%)) | Ammonium salt(g) | Copper salt(g) | A | B |
| 40 | Na$_2$CO$_3$ 4.27 | 6.48 (35.2) | 3.15 (67.7) | 1.08 (23.2) | NH$_4$Cl 1.72 CuCl$_2$ . 2H$_2$O 1.37 | | $\frac{1}{10}$ | 4.0 |
| 41 | K$_2$CO$_3$ 5.55 | 6.26 (37.4) | 3.28 (66.8) | 1.16 (23.4) | NH$_4$Cl 1.72 CuCl$_2$ . 2H$_2$O 1.37 | | $\frac{1}{10}$ | 4.0 |
| 42 | KOH 4.98 | 2.72 (72.8) | 6.37 (66.2) | 2.24 (22.7) | NH$_4$Cl 1.72 CuCl$_2$ . 2H$_2$O 1.37 | | $\frac{1}{10}$ | 4.0 |

Note)
A: Copper salt/Guaiacol (molar ratio)
B: Ammonium salt/Copper salt (molar ratio)

EXAMPLE 43

A mixture of 11.60 g of o-ethoxyphenol, 3.36 g of sodium hydroxide, 7.07 g of allyl chloride, 1.37 g of cupric chloride (CuCl$_2$.2H$_2$O), 1.72 g of ammonium chloride and 34 ml of water was reacted at 25° C and with stirring, for 15 minutes. The reaction solution was then neutralized with hydrochloric acid and extracted with five portions of 30 ml of ether. The resulting ethereal extract was distilled to give 5.17 g of the desired o-ethoxy-p-allylphenol and 5.22 g of the unreacted o-ethoxyphenol. There was also obtained 2.02 g of by-product 1-allyloxy-2-ethoxybenzene.

The conversion was 55.0%, and selectivity to o-ethoxy-p-allylphenol was 62.8%.

EXAMPLE 44

To a solution of 10.00 g of guaiacol and 3.55 g of sodium hydroxide in 30 ml of water were added in order 1.37 g of cupric chloride(CuCl$_2$.2H$_2$O), constituting (A) component of the catalyst, and 0.558 g of hydroxylamine hydrochloride (NH$_2$OH.HCl), constituting (B) component thereof, and 6.80 g of allyl chloride was further added. The mixture was stirred at 20° C and under a nitrogen gas atmosphere, for 60 minutes. The reaction solution was then neutralized with hydrochloric acid and extracted with five portions of 30 ml of ether. The resulting ethereal extract was distilled to give 3.93 g of the desired eugenol and 4.30 g of the unreacted guaiacol. There was also obtained 2.53 g of by-product O-allylguaiacol.

The conversion was 57.0%, and selectivity to eugenol was 52.2%.

COMPARATIVE EXAMPLE 9

A mixture of 10.00 g of guaiacol, 3.22 g of sodium hydroxide, 6.80 g of allyl chloride and 30 ml of water was reacted at 20° C, with stirring and under nitrogen gas atmosphere, for 60 minutes. The reaction solution was then neutralized with hydrochloric acid and extracted with five portions of 30 ml of ether. The resulting ethereal extract was distilled to give 0.54 g of the desired eugenol and 8.17 g of the unreacted guaiacol. There was also obtained 0.94 g of by-product O-allylguaiacol.

The conversion was 18.3%, and selectivity to eugenol was 22.4%.

COMPARATIVE EXAMPLE 10

The reaction stated in Comparative example 9 was repeated except that 1.37 g of cupric chloride was added as a catalyst.

After completion of the reaction, there were obtained 1.83 g of the desired eugenol and 6.64 g of the unreacted guaiacol. There was also obtained 1.98 g of by-product O-allylguaiacol.

The conversion was 33.6%, and selectivity to eugenol was 41.1%.

EXAMPLES 45–49

The procedure stated in Example 44 was repeated except that the conditions set out in Table 8 were adopted. The results are shown in Table 9.

Table 8

| Ex. | Amount of NaOH (g) | Copper-containing compound (g) | | Amount of hydroxylamine hydrochloride (g) |
|---|---|---|---|---|
| 45 | 4.53 | CuCl$_2$ . 2H$_2$O | 1.37 | 2.23 |
| 46 | 5.81 | " | " | 4.47 |
| 47 | 3.66 | " | 0.46 | 0.74 |
| 48 | 4.53 | Cu(CH$_3$COO)$_2$ | 1.46 | 2.23 |
| 49 | " | Cu$_2$O | 1.15 | " |

Table 9

| | Guaiacol | | Eugenol | | O-Allylguaiacol |
|---|---|---|---|---|---|
| Ex. | Recovery (g) | Conversion (%) | Yield (g) | Selectivity (%) | yield (g) |
| 45 | 4.32 | 56.8 | 4.57 | 60.8 | 1.90 |
| 46 | 4.99 | 50.1 | 3.80 | 57.3 | 1.65 |
| 47 | 3.93 | 60.7 | " | 47.3 | 2.96 |
| 48 | 4.26 | 57.4 | 4.08 | 53.8 | 2.50 |
| 49 | 4.18 | 58.2 | 4.07 | 52.9 | 2.62 |

EXAMPLE 50

The reaction stated in Example 44 was repeated except that 11.60 g of o-ethoxyphenol was employed in place of the guaiacol and that the amounts of sodium hydroxide, water, CuCl$_2$.2H$_2$O, hydroxylamine hydrochloride and allyl chloride were respectively changed into 4.70 g, 34 ml, 1.43 g, 2.33 g and 7.07 g.

There were obtained 4.97 g of the desired o-ethoxy-p-allylphenol and 4.99 g of the unreacted 2-ethoxyphenol. There was also obtained 2.31 g of by-product 1-allyloxy-2-ethoxybenzene.

The conversion was 56.9%, and selectivity to the desired compound was 58.4%.

EXAMPLES 51-67

The procedure stated in Example 44 was repeated except that the amount of sodium hydroxide was changed into 3.25 g and that (B) component of the catalyst was chosen as set out in Table 10. The results are shown in Table 10.

Table 10

| Ex. | (B) Component of catalyst (g) | | Conversion (%) | Eugenol Yield (g) | Selectivity (%) | O-allylguaiacol yield (g) |
|---|---|---|---|---|---|---|
| 51 | formamide | 0.73 | 47.5 | 2.92 | 46.5 | 2.43 |
| 52 | " | 1.45 | 62.1 | 4.51 | 54.9 | 2.37 |
| 53 | " | 2.90 | 62.9 | 4.35 | 52.3 | 2.80 |
| 54 | glycine | 1.21 | 62.0 | 4.31 | 52.6 | 2.77 |
| 55 | $\beta$-alanine | 0.72 | 75.8 | 5.61 | 56.0 | 2.84 |
| 56 | " | 1.43 | 71.9 | 5.56 | 58.5 | 1.92 |
| 57 | " | 2.86 | 66.9 | 5.76 | 65.1 | 1.94 |
| 58 | N-methyl-hydrazine | 1.48 | 87.4 | 7.43 | 64.3 | 2.60 |
| 59 | ethylamine* | 4.82 | 54.3 | 4.54 | 63.2 | 1.59 |
| 60 | isopropyl-amine | 1.90 | 49.6 | 3.47 | 52.9 | 2.11 |
| 61 | allylamine | 1.84 | 45.9 | 3.16 | 52.1 | 1.83 |
| 62 | 2-methoxy-ethylamine | 0.605 | 49.7 | 3.49 | 53.1 | 2.14 |
| 63 | " | 1.21 | 59.6 | 4.26 | 54.0 | 2.49 |
| 64 | " | 2.41 | 50.1 | 3.51 | 52.9 | 2.01 |
| 65 | $\epsilon$-amino-caproic acid | 2.11 | 68.4 | 6.22 | 68.8 | 1.49 |
| 66 | hydrazine monohydrate | 1.61 | 70.8 | 5.61 | 59.9 | 2.19 |
| 67 | $\gamma$-amino-n-butyric acid | 1.66 | 59.5 | 4.51 | 57.3 | 2.23 |

*Ethylamine was used in the form of a 30% aqueous solution, and the amount of the solution is set forth here.

EXAMPLE 68

The procedure stated in Example 44 was repeated except that the amount of sodium hydroxide was changed into 3.25 g, that the amount of (A) component of the catalyst, cupric chloride, was changed into 0.457 g, and that 0.805 g of (B) component of 2-methoxyethylamine was added in place of the hydroxylamine hydrochloride.

The conversion was 40.4%, and the yield of eugenol and selectivity to this were 2.39 g and 44.8%, respectively. By-product O-allylguaiacol was also obtained in the yield of 1.65 g.

EXAMPLE 69

The procedure stated in Example 44 was repeated except that the amount of sodium hydroxide was changed into 3.25 g, that 0.65 g of ethylenediamine was added in place of the (B) component of hydroxylamine hydrochloride, and that the reaction period was changed into 15 minutes.

The conversion was 51.6%, and the yield of eugenol and selectivity to this were 3.56 g and 52.2%, respectively. By-product O-allylguaiacol was also obtained in the yield of 2.14 g.

EXAMPLE 70

The procedure stated in Example 44 was repeated except that 1.43 g of $\alpha$-alanine was employed as the (B) component and the reaction period was changed into 180 minutes.

The conversion was 62.1%, and the yield of eugenol and selectivity to this were 4.48 g and 54.5%, respectively. By-product O-allylguaiacol was also obtained in the yield of 2.05 g.

EXAMPLES 71-74

The procedure stated in Example 50 was repeated except that the amount of sodium hydroxide was changed into 3.36 g and the (B) component and its amount were changed as set out in Table 11. The results are shown in Table 11.

Table 11

| Ex. | (B) Component of catalyst (g) | | Conversion (%) | O-Ethoxy-p-allylphenol Yield (g) | Selectivity (%) | 1-Allyloxy-2-ethoxybenzene Yield(g) |
|---|---|---|---|---|---|---|
| 71 | formamide | 1.51 | 60.3 | 4.64 | 51.4 | 3.02 |
| 72 | $\beta$-alanine | 1.49 | 67.2 | 5.74 | 57.1 | 2.36 |
| 73 | 2-methoxy-ethylamine | 2.52 | 49.9 | 3.96 | 53.1 | 2.22 |
| 74 | ethylamine* | 5.04 | 55.0 | 4.39 | 53.3 | 2.23 |

*As for ethylamine, reference is made to Table 10.

EXAMPLE 75

A mixture of 10 g of guaiacol, 6.90 g of allyl chloride, 9.84 g of 28% aqueous ammonia and 34 ml of water was reacted at 25° C and with stirring, for 24 hours. The reaction solution was then neutralized with hydrochloric acid and extracted with five portions of 30 ml of ether. The resulting ethereal extract was distilled to give 2.04 g of the desired eugenol and 6.50 g of the unreacted guaiacol. There was also obtained 2.59 g of by-product O-allylguaiacol. No high-boiling product which could be produced by successive reaction of the eugenol was obtained.

The conversion was 35.0%, and selectivity to eugenol was 44.1%.

COMPARATIVE EXAMPLES 11-13

The procedure stated in Example 75 was repeated except that solid sodium or potassium hydroxide was employed in place of the aqueous ammonia and that the conditions set out in Table 12 were adopted. The results are shown in Table 12.

Table 12

| Com. ex. | Alkali (amount(g)) | | Period (hr) | Conversion (%) | Selectivity to eugenol (%) | High-boiling product(g) |
|---|---|---|---|---|---|---|
| 11 | NaOH | 3.22 | 24 | 50.0 | 34.0 | 2.00 |
| 12 | " | " | 10 | 35.0 | 33.9 | 1.77 |
| 13 | KOH | 4.98 | 24 | 48.0 | 34.0 | 2.20 |

EXAMPLES 76-77

The procedure stated in Example 75 was repeated except that the amount of aqueous ammonia was reduced to half and that the reaction temperature and period were changed as set out in Table 13. The results are shown in Table 13.

Table 13

| Ex. | Aqueous ammonia (g) | Temperature (°C) | Period (hr) | Conversion (%) | Selectivity to eugenol (%) |
|---|---|---|---|---|---|
| 76 | 4.90 | 40 | 24 | 36.9 | 44.0 |
| 77 | " | 25 | 48 | 42.0 | 44.1 |

Note) In these examples, no high-boiling product was produced.

EXAMPLE 78 AND COMPARATIVE EXAMPLE 14

The procedure stated in Example 75 was repeated except that 10.74 g of allyl bromide was employed in place of the allyl chloride and that the reaction conditions set out in Table 14 were adopted. The results are shown in Table 14.

Table 14

| Ex. (Com.) | Alkali (amount(g)) | | Period (hr) | Conversion (%) | Selectivity to eugenol(%) | High-boiling product(g) |
|---|---|---|---|---|---|---|
| 78 | aq. ammonia | 9.84 | 3 | 35.0 | 44.9 | none |
| 14 | NaOH | 3.22 | 3 | 50.0 | 42.9 | 1.76 |

EXAMPLE 79 AND COMPARATIVE EXAMPLE 15

The procedure stated in Example 75 was repeated except that 11.60 g of o-ethoxyphenol was employed in place of the guaiacol, that 6.90 g of allyl chloride was employed, and that the reaction conditions set out in Table 15 were adopted. The results are shown in Table 15.

Table 15

| Ex. (Com.) | Alkali (amount(g)) | | Conversion (%) | Selectivity to o-ethoxy-p-allylphenol(%) | High-boiling product(g) |
|---|---|---|---|---|---|
| 79 | aq. ammonia | 9.90 | 35.0 | 43.9 | none |
| 15 | NaOH | 3.36 | 50.0 | 33.9 | 2.95 |

EXAMPLE 80

A mixture of 10 g of guaiacol, 6.90 g of allyl chloride, 9.84 g of 28% aqueous ammonia, 0.239 g of CuCl and 34 ml of water was reacted at 25° C and with stirring, for 6 hours. The reaction solution was then neutralized with hydrochloric acid and extracted with five portions of 30 ml of ether. The resulting ethereal extract was distilled to give 3.30 g of the desired eugenol and 5.87 g of the unreacted guaiacol. There was also obtained 1.83 g of by-product O-allylguaiacol. Almost no high-boiling product which could be produced by successive reaction of the eugenol was obtained.

The conversion was 41.3%, and selectivity to eugenol was 60.4%.

EXAMPLE 81

The procedure stated in Example 80 was repeated except that no CuCl(catalyst) was added.

The conversion was 10.1%, and selectivity to eugenol was 44.2%. No high-boiling product was formed.

EXAMPLES 82-83

The procedure stated in Example 80 was repeated except that catalyst set out in Table 16 was employed in place of CuCl. The results are shown in Table 16.

Table 16

| Ex. | Catalyst (amount(g)) | | Conversion (%) | Selectivity to eugenol (%) | High-boiling product(%) |
|---|---|---|---|---|---|
| 82 | $CuCl_2 \cdot 2H_2O$ | 0.823 | 30.3 | 60.4 | almost none |
| 83 | $CuBr_2$ | 0.897 | 29.9 | 61.7 | none |

EXAMPLE 84

The procedure stated in Example 80 was repeated except that the amount of aqueous ammonia was changed into 4.92 g and that 0.201 g of $CuSO_4 \cdot 5H_2O$ was employed in place of CuCl.

The conversion was 39.5%, and selectivity to eugenol was 49.2%. Almost no high-boiling product was formed.

EXAMPLE 85

The procedure stated in Example 82 was repeated except that 10.74 g of allyl bromide was employed in place of the allyl chloride and that a 3 hour reaction period was adopted.

The conversion was 54.3%, and selectivity to eugenol was 62.1%. Almost no high-boiling product was given.

EXAMPLE 86

The procedure stated in Example 85 was repeated except that no catalyst was added.

The conversion was 38.5%, and selectivity to eugenol was 45.0%. No high-boiling product was formed.

EXAMPLE 87

The procedure stated in Example 82 was repeated except that 11.60 g of o-ethoxyphenol was employed in place of the guaiacol.

The conversion was 42.5%, and selectivity to o-ethoxy-p-allylphenol was 60.5%. Almost no high-boiling product was formed.

EXAMPLE 88

The procedure stated in Example 87 was repeated except that no $CuCl_2.2H_2O$(catalyst) was added.

The conversion was 11.0%, and selectivity to o-ethoxy-p-allylphenol was 43.6%. No high-boiling product was formed.

What is claimed is:

1. In a process for preparing an o-alkoxy-p-allylphenol in which the alkoxy is methoxy or ethoxy comprising contacting an o-alkoxyphenol in which the alkoxy is as defined above, with an allyl halide in the presence of an aqueous solution of an alkali metal hydroxide, the improvement which comprises employing a copper-containing compound and a nitrogen-containing compound as a catalyst, said copper-containing compound being selected from the group consisting of copper (I) chloride, copper (II) chloride, copper (I) bromide, copper (II) bromide, copper (II) sulfate, copper phosphate, copper acetate and copper oxide, the amount of the copper contained in said copper-containing compound being from 0.01 to 0.2 gram atom per one mole of the o-alkoxyphenol, and the said nitrogen-containing compound being selected from the group consisting of ammonia, ammonium chloride, ammonium phosphate, hydroxylamine hydrochloride, allylamine, an alkylamine having from 1 to 4 carbon atoms, an alkoxyalkylamine having 2 to 4 carbon atoms, an ethylenediamine, a carboxylic acid amide having 1 to 4 carbon atoms, a hydrazine having 0 to 4 carbon atoms and an amino acid, a temperature of from about 0° to about 50° C. being employed when the said nitrogen-containing compound is ammonia and a temperature of from about 0° to about 60° C. being employed when the said nitrogen-containing compound is other than ammonia.

2. The process as claimed in claim 1, wherein the allyl halide is allyl chloride or allyl bromide.

3. The process as claimed in claim 1, wherein the alkali metal hydroxide is sodium hydroxide or potassium hydroxide.

4. The process as claimed in claim 1, wherein the copper-containing compound is a water-soluble copper salt selected from the group consisting of copper (II) chloride, copper (II) bromide and copper (II) acetate.

5. The process as claimed in claim 4, wherein an amount of the copper contained in the water-soluble copper salt is 0.01–0.1 gram atom per one mole of the o-alkoxyphenol.

6. The process as claimed in claim 1, wherein said nitrogen-containing compound is ammonium chloride or ammonium phosphate.

7. The process as claimed in claim 6, wherein the amount of the nitrogen-containing compound is from 1 to 4 moles per one gram atom of the copper.

8. The process as claimed in claim 1, wherein said nitrogen-containing compound is ammonia.

9. The process as claimed in claim 1, wherein said nitrogen-containing compound is selected from the group consisting of hydroxylamine hydrochloride, allylamine, an alkylamine having 1 to 4 carbon atoms, an alkoxyalkylamine having 2 to 4 carbon atoms, ethylenediamine, a carboxylic acid amide having 1 to 4 carbon atoms, a hydrazine having 0 to 4 carbon atoms and an amino acid.

10. The process as claimed in claim 9, wherein the amount of the nitrogen-containing compound is 1–10 moles per one gram atom of the copper contained in the water-soluble salt.

11. The process as claimed in claim 9, wherein the nitrogen-containing compound is selected from the group consisting of ethylamine, glycine, $\beta$-alanine and $\epsilon$-aminocaproic acid.

12. The process as claimed in claim 1, wherein the copper-containing compound is a hydroxide or oxide of copper, and the amount of the copper is 0.01–0.1 gram atom per one mole of the o-alkoxyphenol.

13. The process as claimed in claim 1, wherein said copper-containing compound is $[Cu^{I}(NH_3)_2]Cl$ or $[Cu^{II}(NH_3)_4]Cl_2$.

14. The process as claimed in claim 1, wherein said copper-containing compound is $CuCl_2.2NH_4Cl$.

* * * * *

UNITED STATES PATENT AND TRADEMARK OFFICE
CERTIFICATE OF CORRECTION

PATENT NO. : 4,048,236
DATED : September 13, 1977
INVENTOR(S) : SHIGEKI NAGAI et al It is certified that error appears in the above-identified patent and that said Letters Patent are hereby corrected as shown below:

Column 2, line 4: before "solution", insert --- a ---.

Column 2, line 15, and Column 3, line 21:
   replace "amine" with --- ammine ---.

Column 3, line 11: replace "metay" with --- metal ---.

Column 7, line 20: replace "$[Cu^I(NH_3)_2]^{+\lambda}$" with
   --- $[Cu^I(NH_3)_2]^+$ ---.

Column 8, line 39: replace "...$2H_2O$was" with
   --- ...$2H_2O$ was ---.

Column 14, line 64: replace "Nohigh" with --- No high ---.

Signed and Sealed this

Sixteenth Day of May 1978

[SEAL]

Attest:

RUTH C. MASON
Attesting Officer

LUTRELLE F. PARKER
Acting Commissioner of Patents and Trademarks